United States Patent
Zand et al.

[11] Patent Number: 6,091,336
[45] Date of Patent: Jul. 18, 2000

[54] MOISTURE DETECTION APPARATUS

[75] Inventors: Farnaz Zand, Burbank; Warren M. Haussler, Pasadean, both of Calif.

[73] Assignee: Franz Zand, Burbank, Calif.

[21] Appl. No.: 09/275,103

[22] Filed: Mar. 24, 1999

[51] Int. Cl.$^7$ .................................................. G08B 21/00
[52] U.S. Cl. ...................... 340/604; 340/605; 340/573.5; 200/61.04; 200/61.05; 137/123
[58] Field of Search ..................... 340/604, 603, 340/573.1, 573.5, 605; 137/123; 200/61.04, 61.05

[56] References Cited

U.S. PATENT DOCUMENTS

| | | |
|---|---|---|
| 3,939,360 | 2/1976 | Jackson . |
| 4,106,001 | 8/1978 | Mahoney . |
| 4,191,950 | 3/1980 | Levin et al. . |
| 4,246,575 | 1/1981 | Purtell et al. ............................ 340/605 |
| 4,347,503 | 8/1982 | Uyehara . |
| 4,356,818 | 11/1982 | Marcias et al. . |
| 4,484,573 | 11/1984 | Yoo . |
| 4,539,559 | 9/1985 | Kelly et al. . |
| 5,226,386 | 7/1993 | Thoma . |
| 5,817,081 | 10/1998 | LaVon et al. . |
| 5,959,535 | 9/1999 | Remsburg ................................ 340/604 |

*Primary Examiner*—Julie Lieu
*Attorney, Agent, or Firm*—James E. Brunton, Esq.

[57] ABSTRACT

A moisture detection apparatus for signaling to a caregiver that a diaper or other article of clothing worn by an infant or adult being cared for by the caregiver is wet and needs to be changed. The apparatus includes a liquid transfer component having a plurality of capillaries for transferring liquid from the wet diaper to a remote location and a signaling device which emits either an audio signal or a visual signal, or both when an infant or adult patient is in need of attention due to a wet diaper or other article of clothing.

17 Claims, 3 Drawing Sheets

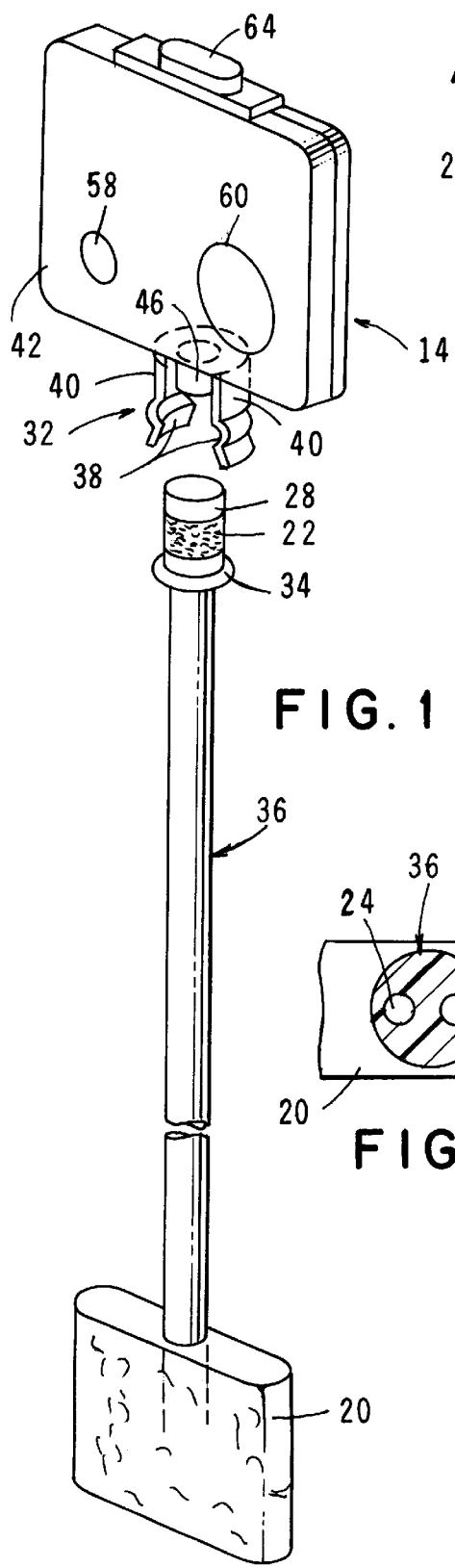
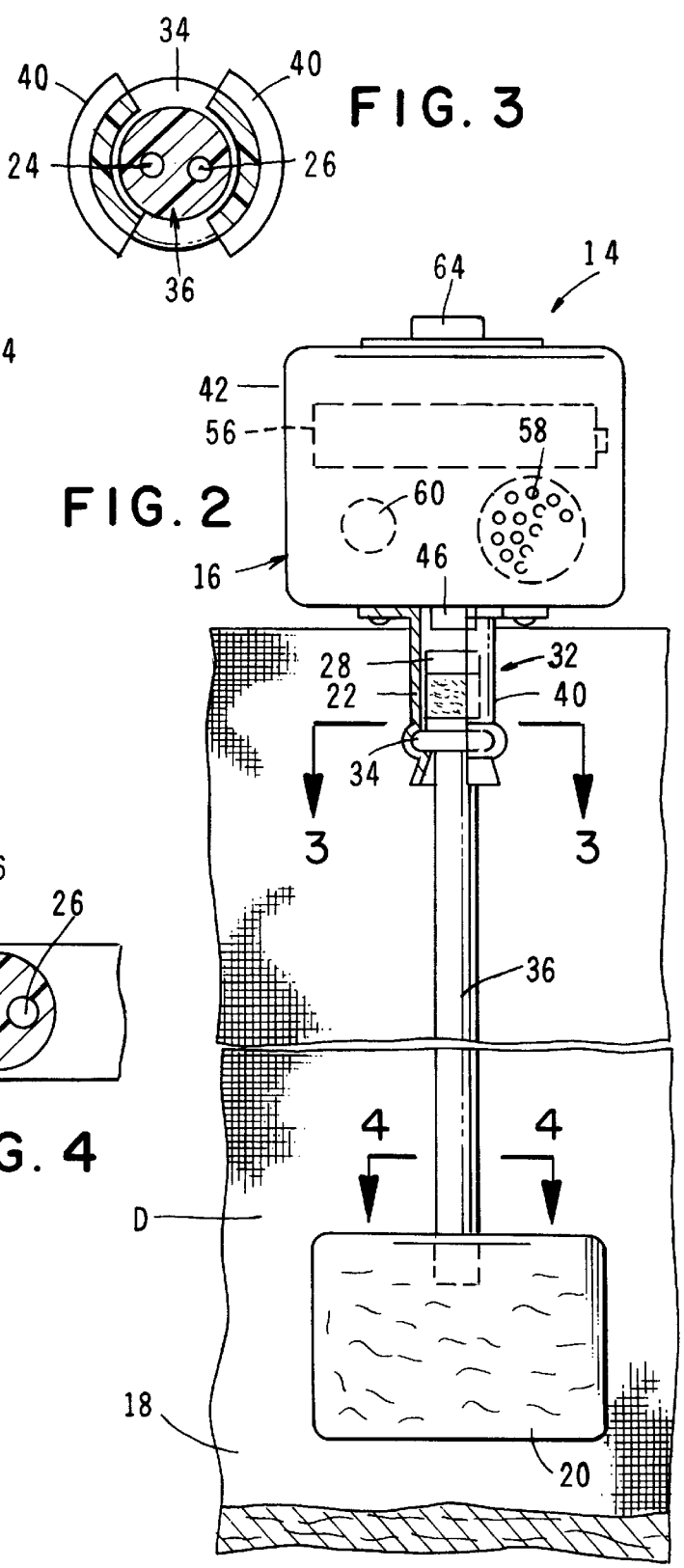

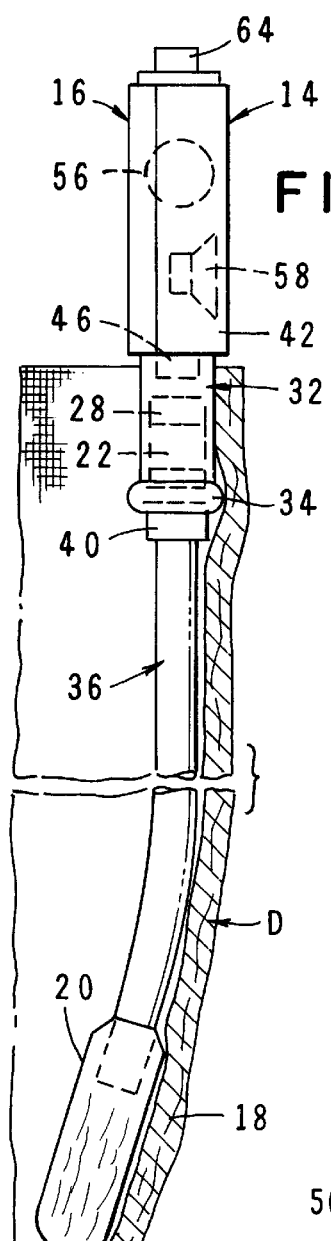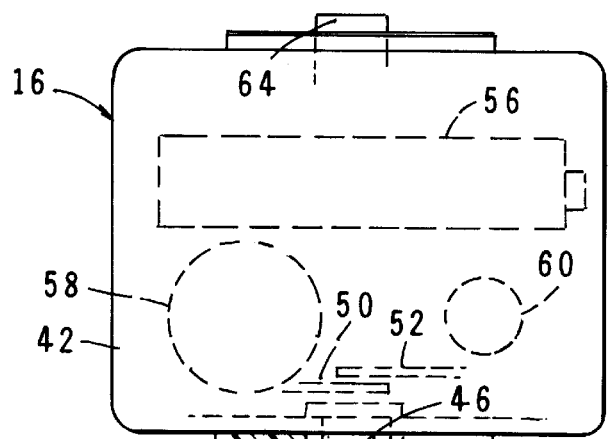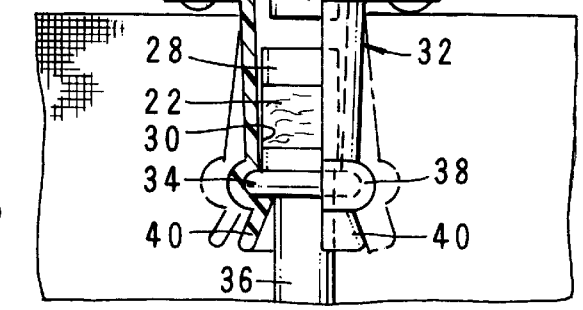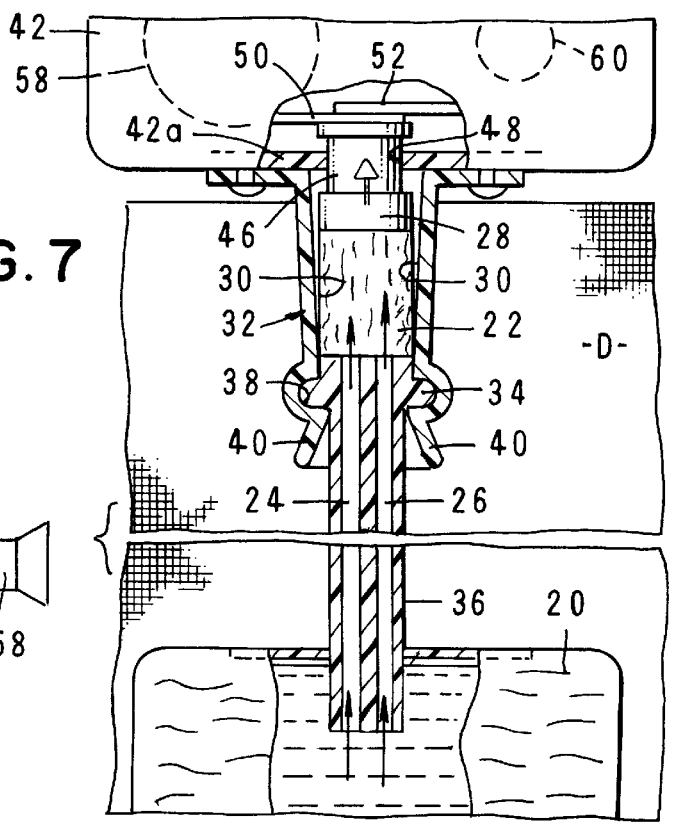
FIG. 5
FIG. 6
FIG. 7
FIG. 8

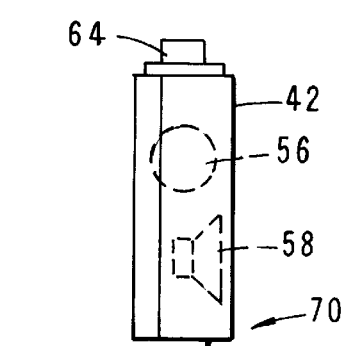
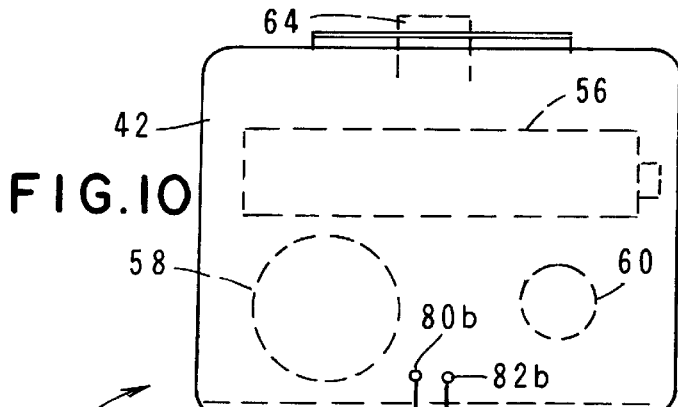
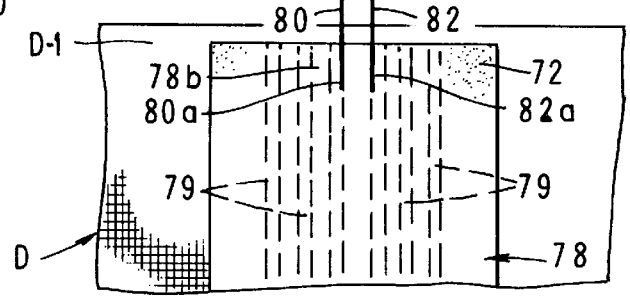
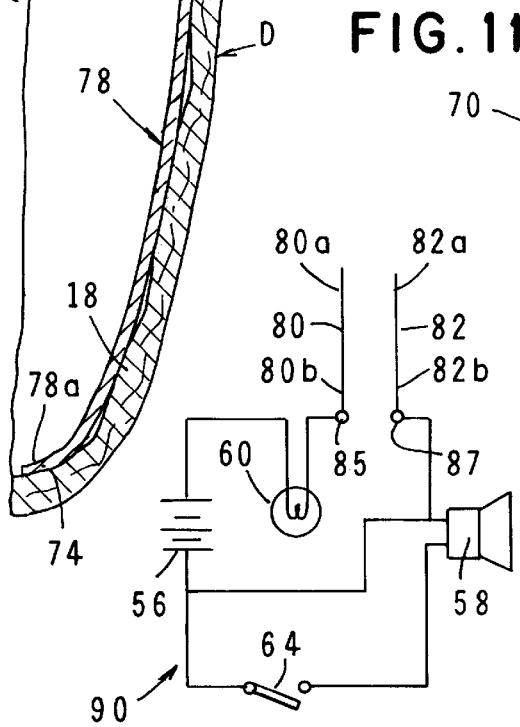
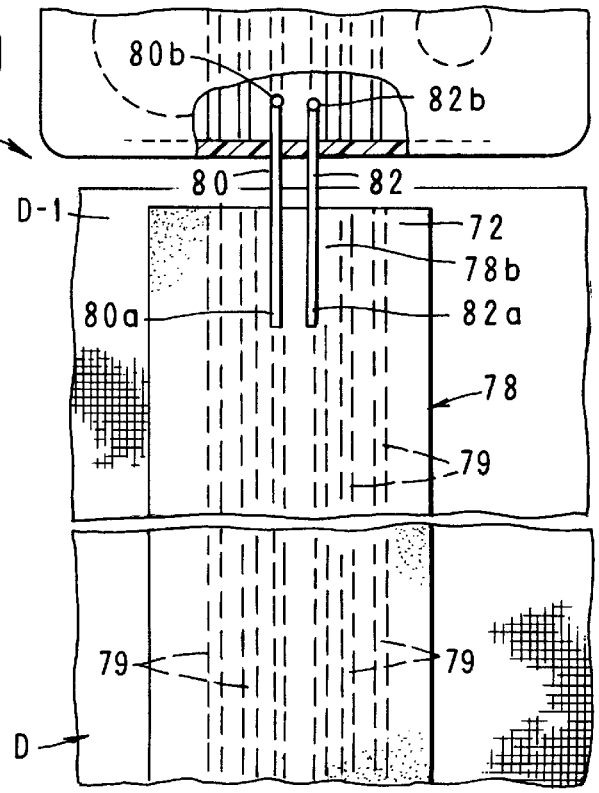

MOISTURE DETECTION APPARATUS

BACKGROUND OF THE INVENTION

1. Field of the Invention

The present invention relates generally to moisture detection devices. More particularly, the invention concerns a novel apparatus for detecting moisture such as that caused by urine in articles of clothing including infant and adult diapers.

2. Discussion of the Prior Art

The common way of determining whether either an infant or adult diaper is wet is for the caregiver to insert his or her hand into the diaper to feel for moisture. This is very unsanitary and, if the caregiver does not immediately wash his or her hands, contamination caused by the exposure of the hands to urine can be spread with possible serious adverse healthy consequences. The present invention is directed to the solution of this serious problem.

There has long been an unsatisfied need in both the home care and hospital environment for a sanitary means of determining whether either an infant or an adult wearer of diapers is in need of a diaper change. Because no suitable means has been developed to alert the caregiver, frequently nothing is done to correct the undesirable condition of a contaminated diaper until the infant cries or the adult patient senses the problem and complains. Even then, if the caregiver is occupied with other pressing matters, the problem cannot be corrected for some period of time.

As will be better understood from the discussion that follows, the novel apparatus of the present invention provides an immediate audio or visual signal to the caregiver that a particular patient or infant is in need of care so that corrective action can be taken in a prompt and orderly fashion. This immediate signaling of a problem is highly beneficial in both the home and hospital envorinment and can avoid the prolonged discomfort of the infant or adult who is the responsibility of the particular caregiver.

SUMMARY OF THE INVENTION

It is an object of the present invention to provide a simple, easy to use and highly reliable moisture detection apparatus for signaling to a care giver that a diaper or other article of clothing worn by an infant or adult being cared for by the caregiver is wet and needs to be changed.

Another object of the invention is to provide an apparatus of the aforementioned character which is unobtrusive and can be conveniently affixed by the caregiver to a diaper or other article of clothing of the person being cared for.

Another object of the invention is to provide a moisture detection apparatus which emits either an audio signal or a visual signal, or both when an infant or adult patient is in need of attention due to a wet diaper or other article of clothing.

Another object of the invention is to provide an apparatus of the class described in the preceding paragraphs which is of an elegantly simple construction and one in which all of the components of the device, save for the signaling device, can be readily disposed of after use.

Another object of the invention is to provide an apparatus of the class described which is compact, comfortable for the user to wear and one which can be inexpensively manufactured.

BRIEF DESCRIPTION OF THE DRAWINGS

FIG. 1 is a generally perspective view of one form of the moisture detection apparatus of the invention.

FIG. 2 is a foreshortened front view of the apparatus of the FIG. 1 shown being used to detect moisture in an article of clothing such as a diaper.

FIG. 3 is a greatly enlarged, cross-sectional view taken along lines 3—3 of FIG. 2.

FIG. 4 is a greatly enlarged, cross-sectional view taken along lines 4—4 of FIG. 1.

FIG. 5 is a foreshortened side-elevational view of the apparatus of FIG. 1 shown as it appears when in position within an article of clothing such as a diaper.

FIG. 6 is an enlarged, fragmentary front view of the apparatus of FIG. 1 partly broken away to show internal construction and to illustrate the manner in which the liquid transfer means or capillaries of the apparatus are interconnected with the signaling means.

FIG. 7 is an enlarged generally front view similar to FIG. 6, but also showing the lower portion of the apparatus and illustrating the operation of the device to close the switch means which energizes the signaling means of the invention.

FIG. 8 is a generally diagrammatic view of one form of the electrical circuitry of the apparatus of the invention.

FIG. 9 is a foreshortened, side-elevational view, partly in cross section of an alternate form of the apparatus of the invention.

FIG. 10 is an enlarged, fragmentary front view of the apparatus of FIG. 9 partly broken away to show internal construction and to illustrate the manner in which the liquid transfer means of this latest form of the apparatus is interconnected with the signaling means.

FIG. 11 is an enlarged fragmentary front view similar to FIG. 10, but also showing the lower portion of the apparatus and illustrating the manner in which the electrical connectors are affixed to the liquid transfer means and to the signaling means.

FIG. 12 is a generally diagrammatic view of an alternate form of the electrical circuitry of the apparatus of this second form of the invention.

DESCRIPTION OF THE INVENTION

Referring to the drawings and particularly to FIGS. 1 through 5, one form of the moisture detection apparatus of the present invention is there illustrated and generally designated by the numeral 14. The apparatus functions to indicate at a first location 16, the existence of moisture caused by the existence of liquid at a second remote location 18 (FIGS. 2 and 5). In the present form of the invention, the apparatus comprises a moisture detection means located proximate the second location 18 for detecting moisture at the second location and a signaling means located proximate the first location. The signaling means is operably interconnected with the detection means and functions to signal the existence of moisture at the second location. Forming a part of the detection means is a liquid transfer means for transferring a small quantity of liquid from the second location 18 to a switch operating means located proximate the detection means. This novel switch operating means functions to operate switch means which also form a part of the detection means of the invention. In a manner presently to be described, the switch means functions to close an electrical circuit upon the detection of moisture at the second location. Upon being closed, the switch means, functions to activate at least one signaling device for indicating the existence of moisture at the second location 18.

In the form of the invention shown in the drawings, the detection means comprises a pad 20 constructed from a first liquid absorbing material. As shown in FIGS. 2 and 5, pad 20 is located proximate the second remote location 18 and is disposed in contact with an article of clothing such as a diaper "D". Diaper "D" which is of conventional construction and may be of a character worn by an infant or by an adult patient in either a home care or hospital environment. The switch operating means of the invention comprises a second pad 22 also constructed from a liquid absorbing expandable material. Pad 22, which is operably associated with the switch means of the invention, functions to close the switch means upon detection of moisture at second locations 18.

Disposed intermediate first and second liquid absorbing materials 18 and 22 is the important liquid transfer means of the invention which here comprises a pair of elongated capillaries 24 and 26. As best seen in FIG. 7, one end of each of the capillaries is in communication with first the absorbing material or pad 20 and the other end of each of the capillaries is in communication with the second absorbing material or pad 22. Affixed to the upper end of pad 22 is a pusher means for moving the contacts of the switch means into conductive engagement. This pusher means here comprises a metal pusher disk 28 which is telescopically movable by pad 22 within a passageway 30 formed in a connector assembly 32 which functions to interconnect the liquid transfer means with the detector means. In this regard, it is to be observed that a generally annular shaped protuberance 34 is formed proximate the upper end of the capillary assembly 36 which comprises capillaries 24 and 26 (see FIGS. 1, 2, and 3). Protuberance 34 is constructed and arranged to be received within grooves 38 formed in a pair of wing-like connector members 40 that are connected to the housing 42 of the signaling means. As indicated in FIG. 6, connector members 40 are constructed from a resiliently deformable material so that they will spring apart as the liquid transfer means is coupled with the connector assembly 32 and will then snap into engagement with protuberance 34 to releasably interconnect the liquid transfer means with the signaling means in the manner shown in FIG. 7. As shown in FIG. 7, when the liquid transfer means is thus connected to the signaling means capillaries 24 and 26 are in direct communication with pad 22.

As also shown by FIGS. 6 and 7, the pusher means of the present form of the invention also includes a second, generally disk-shaped pusher member 46 which is telescopically movable within an opening 48 formed in the bottom wall 42a of housing 42 of the signaling means (FIG. 7). Pusher member 46 is movable between a first position shown in FIG. 6 where it is spaced apart from electrical contacts 50 and 52 of the switch means of the invention to a second position shown in FIG. 7 where it moves into engagement with contact 50 and functions to move contact 50 into conductive engagement with contact 52. In a manner presently to be described, pusher member 46 is moved from the first position shown in FIG. 6 to the second position shown in FIG. 7 by the expansion of pad 22 due to its saturation with liquid flowing through the capillaries 24 and 26 from pad 20.

In addition to the switch means of the invention, the signal generating means also comprises a source of electrical current shown in FIG. 8 as a dry cell battery 56 and first and second signaling devices 58 and 60. In the present form of the invention, signaling device 58 is shown in the form of a audio signaling device while signaling device 60 is shown in the form of an incandescent lamp. These signaling devices, as well as the source of electrical power are housed within housing 42 in the manner shown in FIG. 6. Audio signaling device 58 is of a conventional construction and may comprise any number of readily commercially available signaling sources such as buzzers, horns, sirens, whistles and the like. Similarly, visual light source 60 may comprise commercially available incandescent light bulbs or light emitting diodes. The switch means, the source of electrical current, and the signaling devices are interconnected in a conventional manner as diagrammatically illustrated in FIG. 8. Also forming a part of the electrical circuitry of the apparatus is an on-off switch 64 which is of conventional construction and is used to place the detection means in an operating condition so that closure of contacts 50 and 52 will energize signaling devices 58 and 60. As best seen in FIG. 1, switch 64 is a manually operated switch preferably mounted proximate the top of housing 42.

In using the apparatus of the invention, this disposable portion of the apparatus, namely the assembly made up of pads 20 and 22, pusher member 28 and capillary assembly 36 are positioned within a diaper "D" or similar article of clothing in the manner illustrated in FIGS. 2 and 5. When correctly positioned a within the diaper "D", pad 20 is in engagement with the interior surface of the diaper while housing 42 of the signaling means is disposed at a location above the upper extremity of the diaper "D". As previously mentioned, the signaling means is interconnected with the disposable portion of the apparatus by snapping wing-like members 40 over protuberance 34 of the liquid transfer means. With the components of the apparatus of the invention interconnected in the manner shown in FIGS. 2 and 6, liquid existing in the diaper 18 will be transferred to the liquid absorbing material or pad 20 and will, within in short period of time saturate the small pad 20. When pad 20 becomes saturated, a portion of the liquid which is saturating the pad will be transferred by capillary action through capillaries 24 and 26 to the second absorbing material, or pad 22. As pad 22 absorbs the liquid such as urine, it will expand in the manner shown in FIG. 7 causing pusher member 28 to engage pusher member 46 and move the pusher member from the first position shown in FIG. 6 to the second position shown in FIG. 7. As pusher member 46 is moved into the second position, it will engage one of the electrical contacts such as contact 50 and move it into conductive engagement with the other of the contacts such as contact 52 thereby closing the circuit and activating signaling devices 58 and 60.

Upon actuating signaling devices 58 and 60, both a visual and audio signal will be transmitted to the caregiver notifying the caregiver that attention to the particular patient is required. Signaling by the signaling devices will continue until normally closed switch 64 is opened so as to break the circuit.

Once the diaper or other article of closing has been changed, the disposable portion of the apparatus of the invention can be inexpensively disposed of and a new detection and liquid transfer means can be interconnected with the signal means in the manner shown in FIGS. 5 and 7. Preferably normally closed switch 64 will automatically close so as to ready the device for further signaling. However, if switch 64 is a manually operated switch it can be manually closed following interconnection of the detection means with the liquid transfer means. When the apparatus of the invention is interconnected in the manner show in FIGS. 2 and 6, contacts 50 and 52 will be spaced apart and will remain in a spaced-apart configuration unless and until sufficient liquid is transferred to pad 22 to expand it sufficiently to cause pusher members 28 and 46 to act upon the switch means to close it thereby once again activating the signaling means or signaling devices 58 and 60.

Turning next to FIGS. 9 through 12, an alternate form of the moisture detection apparatus of the present invention is there illustrated and generally designated by the numeral 70. This apparatus is similar in some respects to that shown in FIGS. 1 through 8 and functions to indicate at a first location 72 the existence of moisture caused by the existence of liquid at a second remote location 74 (FIGS. 9 and 11). Because of the similarities between this latest form of the invention and that previously described, like numbers are used in FIGS. 9 through 12 to designate like components. In this second form of the invention, the apparatus comprises a moisture detection means for detecting moisture at the second location and a signaling means located proximate the first location. The signaling means of this second form of the invention is identical to that earlier described, is operably interconnected with the detection means and, as before, functions to signal the existence of moisture at the second location 74.

Forming a part of the detection means of this latest form of the invention is a highly novel liquid transfer means for transferring liquid from the second location 74 to the electrical conduit means of this second form of the invention which is located proximate the first location 72. In a manner presently to be described, the novel detection means functions to close the electrical circuit shown in FIG. 12 upon the detection of moisture at the second location. Upon being closed, at least one signaling device for indicating the existence of moisture at the second location 74 will be energized.

In the form of the invention shown in FIGS. 9 through 11, the liquid transfer means comprises a unique capillary fiber transfer media 78, the character of which will presently be described. As shown in FIG. 9, a portion 78a of the transfer media is located proximate the second remote location 74 and is disposed in contact with the crotch area of an article of clothing such as a diaper "D". Diaper "D" which is of conventional construction and may be of a character worn by an infant or by an adult patient in either a home care or hospital environment.

The novel capillary fiber transfer media 78 of this second form of the invention comprises a unique bonded fiber component sold by Filtrona Richmond, Inc. of Richmond, Virginia under the name and style TRANSPAD. In the present application, this novel bonded fiber component comprises a multiplicity of capillaries 79 which function to efficiently transfer liquid from location 74 to location 72. While various materials can be used to construct the transfer media 78, the media here consists of a multiplicity of bonded, cellulose acetate fibers laid down as an extended fibrous cloth material that is approximately 1.0 millimeter thick. As indicated in FIGS. 9, 10, and 11, the cloth material is laid along a central portion of the diaper "D" so that at least portion 78a will come into contact with liquid deposited onto the crotch area of the diaper. With this construction, the transfer media will efficiently pull liquid from the wet portion of the diaper and quickly and effectively transfer it to location 72 and into proximity with the electrical conduit means which here comprises first and second small diameter, spaced-apart electric wires 80 and 82. Wires 80 and 82 are safely disposed proximate the waist band of the diaper and terminate in the waist band area so as to never come in contact with the heavily saturated crotch portions of the diaper and the highly sensitive areas of the user's body. The wires are also strategically spaced so that, as moisture is transferred to location 72, the electrical conductivity through the media will close the electrical circuit 84 (FIG. 12) actuating the signaling devices 58 and 60. Preferably at least a potential of 9 volts D.C. is provided to initiate electrical conductivity through the moisturized material. Signaling devices 58 and 60 of the signal generating means are identical in construction and operation to those previously described.

As before, the signal generating means of the invention also comprises a source of electrical current shown in FIG. 12 as a dry cell battery 56 as well as first and second signaling devices 58 and 60. Signaling device 58 is here shown in the form of an audio signaling device while signaling device 60 is shown in the form of an incandescent lamp. Electric wires 80 and 82, the source of electrical current, and the signaling devices are interconnected in a conventional manner as diagrammatically illustrated in FIG. 12. Also forming a part of the electrical circuitry of the apparatus is the previously identified on-off switch 64 which is of a conventional construction and is used to place the detection means in an operating condition so that the transfer of liquid to location 72 will energize signaling devices 58 and 60.

In using the apparatus of the invention, this disposable portion of the apparatus, namely the assembly made up of transfer media 78 and electrical wires 80 and 82 which are positioned within the waistband area D-1 of a diaper "D" or similar article of clothing in the manner illustrated in FIGS. 9. 10, and 11. When correctly positioned within the diaper "D", media 78 is in engagement with the interior surface of the diaper while housing 42 of the signaling means is disposed at a location above the upper extremity of the diaper "D". As previously mentioned, wires 80 and 82 safely terminate at ends 80a and 82a and do not extend below the waist band area D-1 of the diaper. The signaling means is readily interconnected with the disposable portion of the apparatus by interconnecting the upper ends 80b and 82b of wires 80 and 82 with contacts 85 and 87 of circuit 90 in the manner shown in FIG. 12.

During use of the apparatus of the invention, liquid existing in the crotch area of the diaper 18 will be transferred to location 72 by the novel capillary action of fiber media 78 via the multiplicity of capillaries 79. As area location 78b of the transfer media becomes saturated, current will flow between electrical wires 80 and 82 closing the circuit and activating signaling devices 58 and 60.

Upon actuation of signaling devices 58 and 60, both a visual and audio signal will be transmitted to the caregiver notifying the caregiver that attention to the particular patient is required. Signaling by the signaling devices will continue until normally closed switch 64 is opened so as to break the circuit.

Once the diaper or other article of clothing has been changed, the disposable portion of the apparatus of the invention, including the transfer media 78 can be inexpensively disposed of and a new liquid transfer means can be interconnected with the signaling means in the manner shown in FIGS. 9, 10, and 11. Preferably normally closed switch 64 will automatically close so as to ready the device for further signaling. However, if switch 64 is a manually operated switch it can be manually closed following interconnection of the signaling means with the detection means. When the apparatus of the invention is interconnected in the manner show in FIGS. 10 and 11, circuit 90 will remain open unless and until sufficient liquid is transferred to location 72 to actuate the signaling means or signaling devices 58 and 60.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A moisture detection apparatus for detecting at a first location the presence of moisture within a liquid absorbing material disposed at said first location caused by the existence of a liquid at a second remote location, said apparatus comprising:

(a) detection means, including liquid transfer means disposed intermediate said first and second locations, for absorbing moisture at said second location and for transferring the moisture to the first location, said detection means comprising a first liquid absorbing material disposed at the second location, said liquid transfer means comprising non-absorbing means for transferring liquid from said first liquid absorbing material to said liquid absorbing material located at said fist location in a quantity sufficient to cause said liquid absorbing material to become electrically conductive;

(b) signaling means located proximate said first location and operably associated with said detection means for emitting a signal upon said liquid transfer means transferring liquid to said first location.

2. The apparatus as defined in claim 1 in which said liquid transfer means comprises a pair of elongated capillary tubes.

3. An apparatus for indicating at a first location the existence of moisture caused by the disposition of a liquid at a second remote location, said apparatus comprising:

(a) a first liquid absorbing material disposed at the second remote location;

(b) a second liquid absorbing expandable material disposed proximate the first location;

(c) a liquid transfer means comprising a plurality of capillaries disposed intermediate said first and second liquid absorbing materials for transferring liquid from said first liquid absorbing material to said second liquid absorbing material in a quantity sufficient to cause said second liquid absorbing material to expand; and (d) a signal generating means operably associated with said second liquid absorbing material for generating a signal upon expansion of said second liquid absorbing material.

4. A device as defined in claim 3 in which said liquid transfer means comprises at least one capillary extending between said first and second liquid absorbing materials.

5. A device as defined in claim 3 in which said signal generating means generates an audio signal.

6. A device as defined in claim 3 in which said signal generating means generates a visual signal.

7. A device as defined in claim 3 in which said signal generating means comprises:

(a) a source of electrical current;

(b) a signaling device connected to and operated by said source of electrical current; and (c) switch means disposed between said signal and said source of electrical current for controlling the flow of current therebetween.

8. A device as defined in claim 7 in which said switch means comprises a first contact connected to said signaling device and a second contact connected to said source of electrical current, one of said first and second contacts being movable into engagement with the other of said first and second contact by the expansion of said second liquid absorbing material.

9. A moisture detection apparatus for detecting moisture within a liquid absorbing material disposed at a first location, the presence of moisture caused by the existence of a liquid within a liquid absorbing material located at a second remote location, said apparatus comprising:

(a) detection means including liquid transfer means for absorbing moisture at said second location and for transferring the moisture to the first location, said liquid transfer means comprising a multiplicity of capillaries; and (b) signaling means located proximate said first location and operably associated with said detection means for emitting a signal upon said liquid transfer means transferring moisture to said first location, said signaling means comprising:

(i) a source of electrical current comprising a battery; and (ii) a signalling device connected to and operated by said source of electrical current.

10. The apparatus as defined in claim 9 in which said detection means comprises a pair of electrical wires connected to said liquid transfer means and terminating at said first location and in which said signaling means comprises:

(a) a first contact connected to one of said pair of electrical wires; and (b) a second contact connected to the other of said pair of electrical wires.

11. The apparatus as defined in claim 10 in which said liquid transfer means comprises a fiber bonded transfer media within which said multiplicity of capillaries are formed.

12. The apparatus as defined in claim 11 in which said fiber bonded transfer media comprises a multiplicity of bonded, cellulose acetate fibers.

13. A moisture detection apparatus for detecting at a first location the presence of moisture caused by the existence of a liquid at a second remote location, said apparatus comprising:

(a) detection means, including liquid transfer means, for absorbing moisture at said second location and for transferring the moisture to the first location, said detection means further comprising a first liquid absorbing material disposed at said second location; said liquid transfer means comprising a pair of elongated capillary tubes;

(b) signaling means located proximate said first location and operably associated with said detection means for emitting a signal upon said liquid transfer means transferring moisture to said first location, said signaling means comprising:

(i) a source of electrical current;

(ii) a signaling device connected to and operated by said source of electrical current; and (iii) switch means disposed between said signalling means and said source of electrical current for controlling the flow of current there between, said switch means comprising:

a. a first contact connected to said signaling device;

b. a second contact connected to said source of electrical current and spaced apart from said first contact; and c. switch operating means for moving said first and second contacts into conductive engagement, said switch operating means comprising a second liquid absorbing, expandable material in communication with said liquid transfer means.

14. The apparatus as defined in claim 13 in which said liquid transfer means comprises a pair of elongated capillary tubes extending from said signaling means to said first liquid absorbing material.

15. The apparatus as defined in claim 14 in which said switch means further comprises pusher means disposed between said second liquid absorbing, expandable material and one of said first and second contacts for moving said contacts into conductive engagement upon expansion of said second liquid absorbing expandable material.

16. A device as defined in claim 14 in which said signal generating means generates an audio signal.

17. A device as defined in claim 14 in which said signal generating means generates a visual signal.

* * * * *